(12) United States Patent  (10) Patent No.: US 8,612,749 B2
Brown  (45) Date of Patent: Dec. 17, 2013

(54) MEDICAL DEVICE RIGHTS AND RECALL MANAGEMENT SYSTEM

(75) Inventor: Stephen J. Brown, Woodside, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 1178 days.

(21) Appl. No.: 12/117,114

(22) Filed: May 8, 2008
(Under 37 CFR 1.47)

(65) Prior Publication Data

US 2009/0282244 A1    Nov. 12, 2009

(51) Int. Cl.
*H04L 29/06*    (2006.01)
*H04L 9/32*    (2006.01)

(52) U.S. Cl.
CPC .................................. *H04L 9/3294* (2013.01)
USPC ........................................................ 713/158

(58) Field of Classification Search
USPC ................. 726/4, 17, 21, 27, 29; 713/158
See application file for complete search history.

(56) References Cited

U.S. PATENT DOCUMENTS

| | | | |
|---|---|---|---|
| 5,629,980 A | 5/1997 | Stefik et al. | |
| 5,862,803 A * | 1/1999 | Besson et al. | 600/508 |
| 6,088,618 A | 7/2000 | Kerver | |
| 6,772,340 B1 | 8/2004 | Peinado et al. | |
| 6,850,252 B1 | 2/2005 | Hoffberg | |
| 6,895,503 B2 | 5/2005 | Tadayon et al. | |
| 7,080,043 B2 | 7/2006 | Chase et al. | |
| 7,093,296 B2 | 8/2006 | Nusser et al. | |
| 7,095,854 B1 | 8/2006 | Ginter et al. | |
| 2002/0002674 A1 | 1/2002 | Grimes et al. | |
| 2002/0010679 A1 | 1/2002 | Felsher | |
| 2002/0065784 A1 | 5/2002 | Ranzini et al. | |
| 2002/0188214 A1 * | 12/2002 | Misczynski et al. | 600/516 |
| 2003/0065642 A1 | 4/2003 | Zee | |
| 2003/0078853 A1 | 4/2003 | Peinado et al. | |
| 2003/0110133 A1 | 6/2003 | Maritzen et al. | |
| 2003/0204638 A1 * | 10/2003 | Murray | 709/310 |
| 2003/0217011 A1 | 11/2003 | Peinado et al. | |
| 2004/0073803 A1 | 4/2004 | Keramane | |
| 2004/0088541 A1 | 5/2004 | Messerges et al. | |
| 2004/0148503 A1 | 7/2004 | Sidman | |
| 2004/0181490 A1 | 9/2004 | Gordon et al. | |
| 2004/0253942 A1 | 12/2004 | Mowry et al. | |
| 2005/0004873 A1 | 1/2005 | Pou et al. | |
| 2005/0138400 A1 | 6/2005 | Wu et al. | |
| 2005/0149450 A1 | 7/2005 | Stefik et al. | |
| 2005/0273629 A1 | 12/2005 | Abrams et al. | |

(Continued)

FOREIGN PATENT DOCUMENTS

EP    0558975    9/1993
EP    08131551    12/1997

(Continued)

*Primary Examiner* — Peter Shaw
(74) *Attorney, Agent, or Firm* — Suiter Swantz pc llo (57) ABSTRACT

The embodiments provide systems and methods for medical device rights and recall management system. A digital IP rights and recall management device activates a central key server to authenticate software contents and services operated on a microprocessor based medical devices through a coding key that may be embedded in a medical device or in a service provider server or in an end user computer. The recall management server unlocks the software content transmitted from or to a value-added service provider and selectively recall the value-added software component without requiring any physical recall of the medical device. The system maintains a virtual device master record which enables quality control and recall capability for software elements independent of any physical hardware recall.

13 Claims, 9 Drawing Sheets

(56) References Cited

U.S. PATENT DOCUMENTS

| | | |
|---|---|---|
| 2006/0143461 A1 | 6/2006 | Park |
| 2006/0155651 A1 | 7/2006 | Oh et al. |
| 2006/0167882 A1 | 7/2006 | Aydar et al. |
| 2006/0200253 A1 | 9/2006 | Hoffberg et al. |
| 2006/0242074 A1 | 10/2006 | Kokkinen |
| 2008/0221924 A1* | 9/2008 | Ilkin ................................ 705/2 |
| 2008/0285758 A1* | 11/2008 | Chuprov et al. .............. 380/278 |
| 2009/0055320 A1* | 2/2009 | Goertler et al. ................. 705/59 |
| 2009/0249494 A1* | 10/2009 | Disciascio et al. .............. 726/31 |

FOREIGN PATENT DOCUMENTS

| | | |
|---|---|---|
| JP | 54146633 | 11/1979 |
| JP | 5155024 | 6/1993 |
| JP | 5266002 | 10/1993 |
| WO | WO-9636923 | 11/1996 |

\* cited by examiner

MEDICAL DEVICE RIGHTS AND RECALL MANAGEMENT SYSTEM

BACKGROUND

1. Technical Field

The embodiments herein generally relate to field of Digital Rights Management (DRM), and, more specifically to a system and method for management and security of complex content in an electronic distribution system. The embodiments herein also relate to tracking and recalling software and content from multiple third party content providers.

2. Description of the Related Art

Communication devices and the Internet have changed the way people communicate, learn and utilize resources. A wide range of digital information is shared and used by millions of electronic appliances for various purposes. The authors and marketers of content for electronic appliances include database providers, software developers, publishers, recording companies etc. Many third party service providers use content for various devices and for different purposes. Secure and controlled use of digital information and digital rights management is matter of great importance in this electronic age. Many protection techniques have been developed for controlling and managing the different types of content and digital information.

Advanced medical devices are increasingly controlled by software. Many value-added functions such as remote monitoring, patient guidance, education and feedback are integrated with the use of different software in the medical device. These software-based medical devices integrate third party content and third party hardware platforms. Patients have a wide range of medical needs and comorbidities, and may need content to be integrated from a variety of sources. These value-added features and services may be provided by third parties other than the device manufacturer or primary service provider. In addition, the value-added software providers may be the intellectual property holders who license original device manufacturers to make devices that can operate the software.

Existing Digital Rights Management (DRM) solutions protect the rights of singular content providers in electronic distribution systems, but are not adequate to manage complex content that may be integrated from and modified by a variety of content providers. There are no means of tracking and recalling software and content from multiple third party content providers that is modified and adapted by a range of healthcare experts for users with a range of medical conditions and comorbidities.

Consequently, there is a need for developing a system and method where the rights of content creators may be protected. There is a need for system which enables software developers and value-added service providers to manage digital rights to ensure payment for their software-based intellectual property and to enable the quality assurance and potential recall of software components independent of any physical device recall, particularly in an environment where software may operate on hardware platforms from multiple manufacturers.

OBJECTIVE

Primary object of the embodiments herein is to provide a system that enables third party software developers and value-added service providers to manage digital rights.

Another object of the embodiments herein is to track and manage rights and recall status of medical content in medical devices without recalling hardware in case of software failure.

Another object of the embodiments herein is to provide a methodology for ensuring systematic payment to the authors of software-based intellectual property.

Another object of the embodiments herein is to ensure that the information is transmitted and used only in authorized ways, maintaining security and confidentiality.

Yet another object of the embodiments herein is to provide quality assurance by managing potential recalls of software components independent of any physical device recall.

Yet another object of the embodiments herein is to provide a system that enables third party software developers and value-added service providers to manage digital rights, specifically in the medical and healthcare domain where information is particularly sensitive.

Yet another object of the embodiments herein is to provide a Digital Rights Management (DRM) tool used for content that is sent to third party medical devices by service providers.

Yet another object of the embodiments herein is to provide a DRM system wherein every transaction with the content can be tracked and managed by third parties without their access to patient data or the content.

Yet another object of the embodiments herein is to provide a system that is capable of tracking, managing and enforcing a recall from a central server even though multiple service providers are using content in multiple locations and programs.

Yet another object of the embodiments herein is to provide a system that ensures that the content author always gets credit in form of economic value for the product/service rendered even though the content is distributed through many different service providers.

Yet another object of the embodiments herein is to provide an authentication system for governing the operation of medical device rights and recall management where authentication can be done either on the medical device, the server or the service provider's computer.

SUMMARY

In view of the foregoing, the embodiments herein provide a medical device rights and recall management system that enables third party software developers and value-added service providers to manage digital rights to ensure payment for their software-based intellectual property and to enable the recall of software components independent of any physical device recall. It should be appreciated that the embodiments herein may be implemented in numerous ways, including: a process, a system, a device, a method, or any combination thereof.

The system enables the management of software-based medical devices where the medical device is regulated by government authorities for quality while ensuring complete privacy for patients. The content performing the elements of clinical function in medical device may come from a third party developer and is distributed through multiple service providers rather than from the device manufacturer. Every transaction with the content is tracked and managed by third parties who are not allowed to access patient data or the content itself, as the content is populated with a personal patient data.

Additionally, the embodiments herein also describe a recall management system to enable recall of software components independent of a physical device recall, a recall may be demanded by a regulatory agency or if a failure is found in the software. Since a content author registers software content with a key server, the system maintains a virtual master device master record for all software components regardless of service provider who uses content. As each of the service provider servers, the remote devices, and the caregiver computers must register and obtain a key from the key server, the recall management system of the embodiment herein is able to track, manage and enforce a recall management operation. The system is able to track, manage and recall the software content and the services, even when the multiple service providers are using the content in multiple locations and programs. The system also ensures that content author always gets credit in terms of money value, even though the software content is distributed through many different service providers.

The system has a microprocessor based medical device to collect a patient data based on software content supplied from third party service provider. A key server authenticates software and services running on the microprocessor based medical device through a coding key which is embedded in a medical device or in the service provider server or in the end user computer. A device IP and recall manager is connected to the microprocessor based medical device through the key server and a service provider device, to validate a coding key and to enable the service provider to unlock the software contents transmitted to the microprocessor based medical device to selectively recall the value-added software components without requiring a physical recall of the medical device.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be readily understood by the following detailed description in conjunction with the accompanying drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Embodiments herein provide a medical device rights and recall management system that enables third party software developers and value-added service providers to manage digital rights to ensure payment for their software-based intellectual property and to enable the recall of software components independent of any physical device recall.

According to one embodiment herein, the medical device rights and recall management system is a network-based service operating on a key server used to authenticate the software and the services running on a microprocessor-based medical device by means of a coding key that is embedded in the medical device or the service provider server or the end user computer. In one embodiment, the microprocessor based medical devices or remote patient monitoring platforms are embedded with a coding key. A patient monitoring and management system communicates with a key server to unlock software service components. The key server is connected to the medical device through a server attached to the value-added service provider. When the medical device is connected to the network services for value-added software, remotely programmed content, or remote monitoring and data collection services, the key code is transmitted to the key server. The service provider server then authenticates the service through a central key server operated by the digital and recall management provider who validates the key and enables the medical device to unlock the content transmitted from to or from the value-added service provider. The system is also used to selectively recall the value-added software components without requiring any physical recall of the device.

The medical is authenticated by the key server directly or through the service provider or through the server connected to the service provider to transfer a coding key to unlock the software components and the services received from the value-added service provider.

The embodiments herein also describe a recall management system to enable the recall of software components independently without the recall of any physical device, whenever a recall may be demanded by a regulatory agency or a failure is found in the software that needs to be corrected or disabled. Since a content author registers software content with a key server, the system keeps a virtual master device master record for all software components regardless of the service provider who uses the content. Because each of the service provider servers, remote devices, and caregiver computers must register and obtain a key from the key server, it is possible to track, manage and enforce a recall operation even though multiple service providers are using the content in multiple locations and programs.

Figure 1:
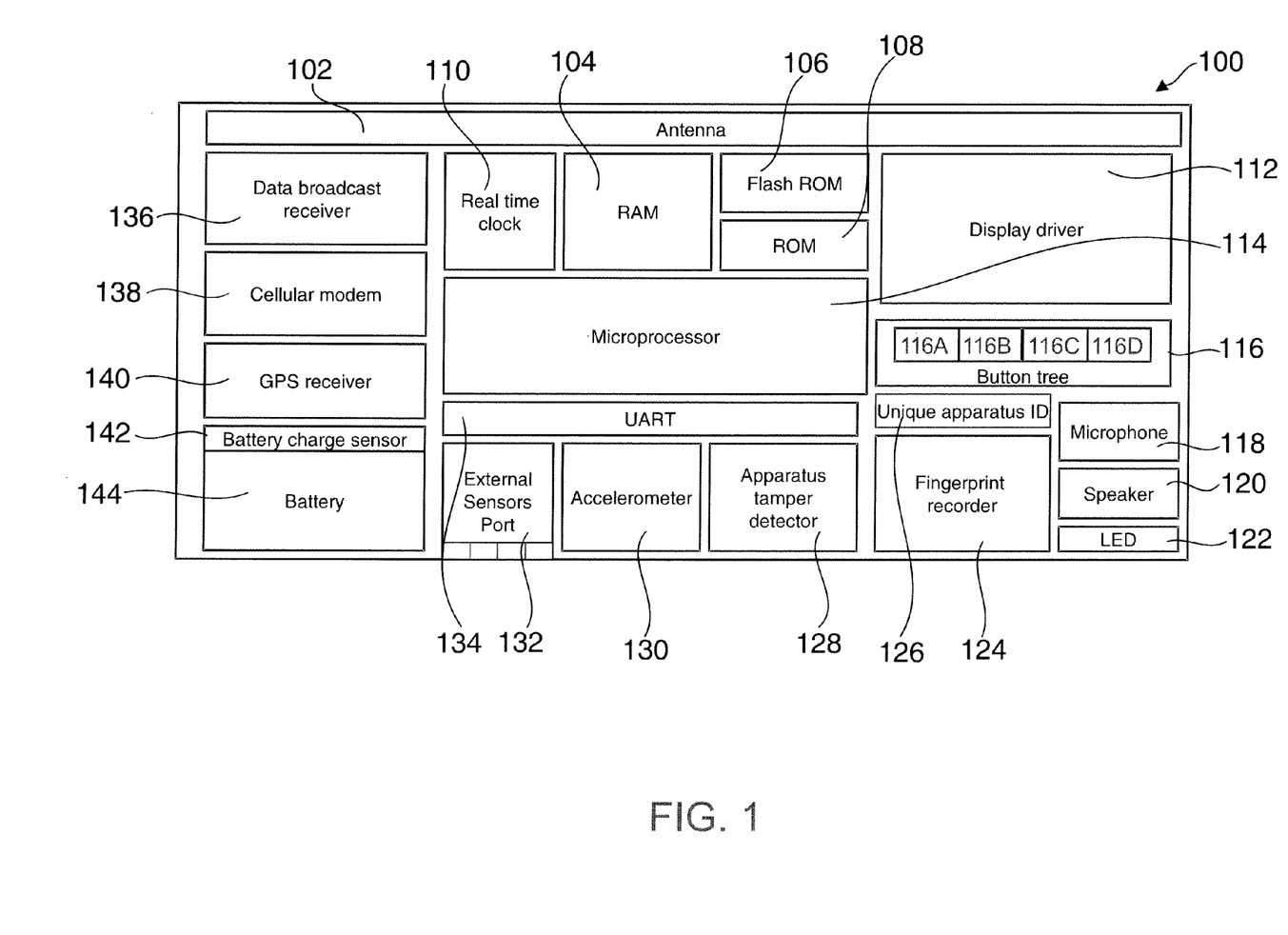
FIG. 1 illustrates a block diagram of a remotely programmable microprocessor-based medical device according to an embodiment herein.

FIG. 1 shows a block diagram of a remotely programmable microprocessor based medical device 100. Device 100 has a microprocessor 114 connected to a memory such as RAM 104, flash ROM 106 and ROM 108 that store program instructions, content and patient data collected through sensors attached to external sensor port 132 or data collected based on a user's interaction with the content through button tree 116. The collected patient data are transmitted to an external server and data base system through a cellular model 138 and antenna 102. Device 100 receives the software contents from a service provider through data broadcast receiver 136. A user inputs data and resets device 100 through buttons 116 A-116 D provided in button tree 116. A remote device authenticates medical device 100 and supplies software content based on unique device identification code 126. The data collected by medical device 100 is transmitted through a cellular modem 138 with a remote server and database management system. A Global Positioning System (GPS) receiver 140 collects GPS position data from a GPS system or a GPS satellite. The user of device 100 is authenticated by finger print recorder 124. The functional components in module 100 are supplied with an electrical power provided from the battery 144. Battery charge sensor 142 detects the residual charge in battery 144 and the detected residual battery charge condition is displayed through LED display 122. Medical device 100 has accelerometer/motion detector 130 which functions as a movement sensor. The data received from the sensors are stored along with the time data received from a real time clock 110. Universal asynchronous receiver/transmitter (UART) 134 is provided to perform a serial communication between microprocessor 114 and the peripheral units attached to medical device 100. An apparatus tamper detector senses the tampering of medical device 100 to output an audio alarm through speaker 120 and a visual alarm through display driver 112. Microphone 118 is provided to receive an audio input to medical device 100.

Figure 2:
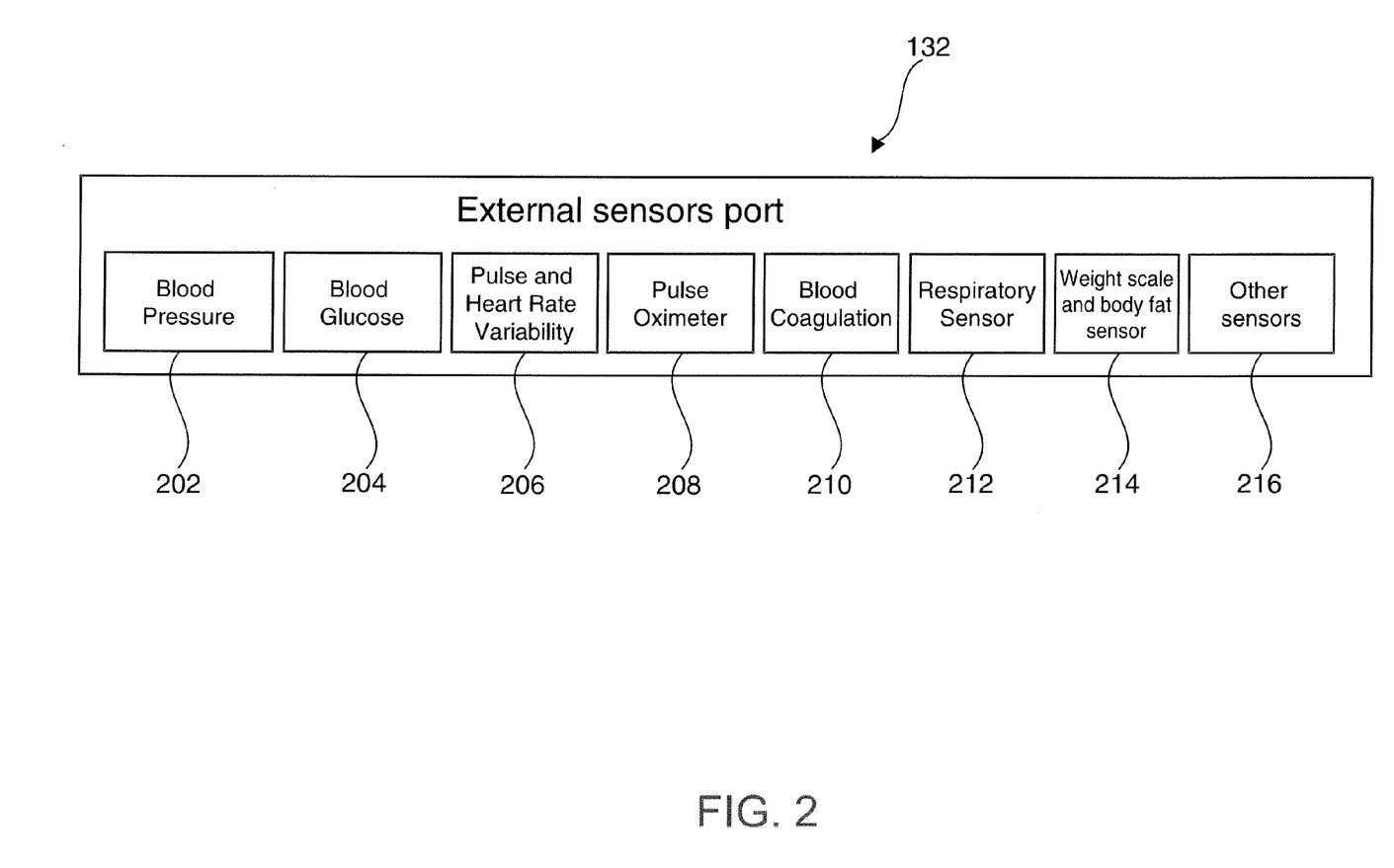
FIG. 2 illustrates the block diagram of the sensors that may be embedded in or connected to external sensor port for value-added services with in the medical device according to an embodiment herein.

FIG. 2 shows types of sensors 202-216 that may be embedded in external sensor port 132 for value-added services with in the medical device. Different types of sensors 202-216 may be coupled to external sensor port 132. The plurality of sensors include blood pressure monitor 202, blood glucose level monitor 204, pulse and heart rate variability monitor 206, pulse oximeter device 208, blood coagulation monitor 210, respiratory sensor 212, weight scale and body fat sensor 214 and other sensor like smoke detector, fire alarm detector, gas leak sensor, humidity sensor etc., that are provided to measure blood pressure level, blood glucose level, pulse and heart rate, blood coagulation condition, respiratory condition, body weight and body fat content of a patient and the smoke, fire break out, gas leak, humidity level of an environment. The sensors detect objective parameters without the need for a user interaction, except in some instances where the user activates or is prompted to activate sensor port 132.

Figure 3:
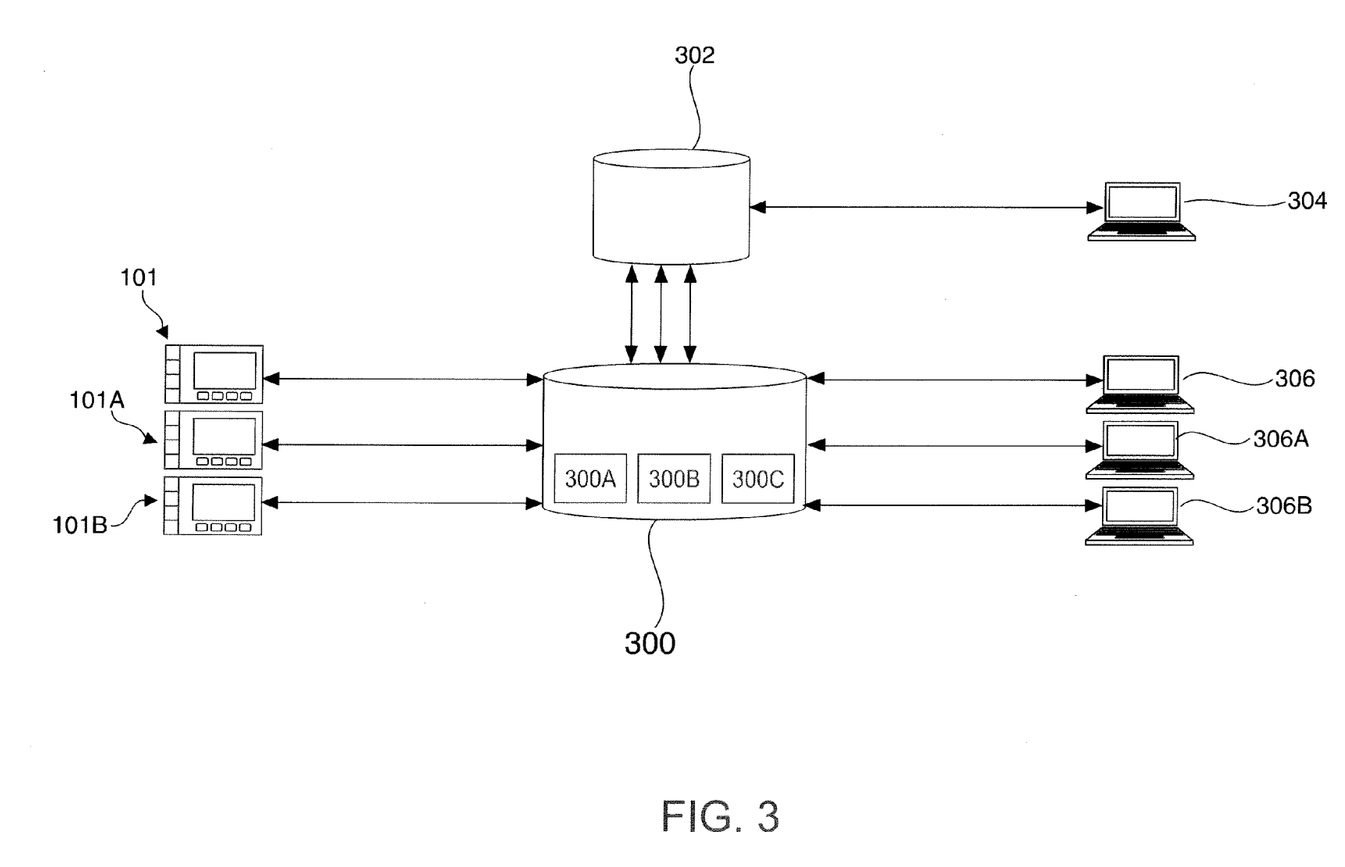
FIG. 3 illustrates a block diagram of a server-based authentication system for governing the operation of medical device rights and recall management system according to an embodiment herein.

FIG. 3 illustrates a server-based authentication system for governing the operation of medical device rights and recall management. Server and database system 300 includes database 300 A for storing data collected by survey device and sensors interface 101, reference database 300 B or databases for storing survey content and application server 300 C with service applications that may access the collected data and a reference database in order to analyze and report information and to communicate new survey content and feedback to survey device 101. Medical device interface 132 is coupled with survey and sensor interface 101 that has a user interface capable of displaying or audibly indicating a text message with a plurality of response choices. The user enters a response to a survey through a button press or through an audible response. The survey and sensor device 101 collects data from the sensors which are coupled to the survey device through a sensor interface 132.

As shown in FIG. 3, a network of value-added device service providers and their customers 306, 306 A, 306 B is also connected to the server and database system 300. System 300 is coupled with key server 302 that is used to authenticate software and services running on the medical device 100 by means of a coding key that is embedded in medical device 100 or in service provider server 300 or in end user computer 306. Medical device 100 or remote patient monitoring platforms may embed this coding key in their design, and the patient monitoring and management system communicates with key server 302 to unlock and decode software service components. Key Server 302 is further connected to Device IP and recall manager 304. When device 101 connects to network services for value-added software, remotely programmed content, or remote monitoring and data collection services, this embedded key code is transmitted to key server 302. Service provider server 300, then authenticates the software content and the services through key server 302 operated by the digital and recall management provider 304. Digital and recall management provider 304 validates the key and enables device 101 to unlock the content transmitted to or from the value-added service provider server 300. The Key server 302 holds the rules for how content can be used, by whom, and whether or not content needs to be turned off or recalled because of a failure.

Survey device 101 has a unique device identification code. The identification code indicates which services device 101 is eligible to receive. Survey device 101 has memory for storing survey content that is intended for that specific device based on its unique identification code and its services identifier. The messages are transmitted over the network between device 101 and server 300 with a combination of coding for intended recipient and content. Each message portion indicates the unique intended recipient and indicates subscriber service type. The message portion includes survey content and other commands and instructions to organize survey into a script.

Service provider server 300 may selectively recall value-added software components without requiring any physical recall of device 101, which may have come from any one of a plurality of licensed manufacturers of compatible devices. This is especially important as most of the device intellectual property is software based and most of the device manufacturing and supply is outsourced and licensed to original device manufacturers. Service provider server 300 may maintain a virtual device master record which enables quality control and recall capability for software elements independent of any physical hardware recall. Service provider server 300 may also ensures that every transaction with the content is tracked and managed by the third parties without allowing them to access the patient data or the content itself as the content is populated with personal patient data.

Figure 4:
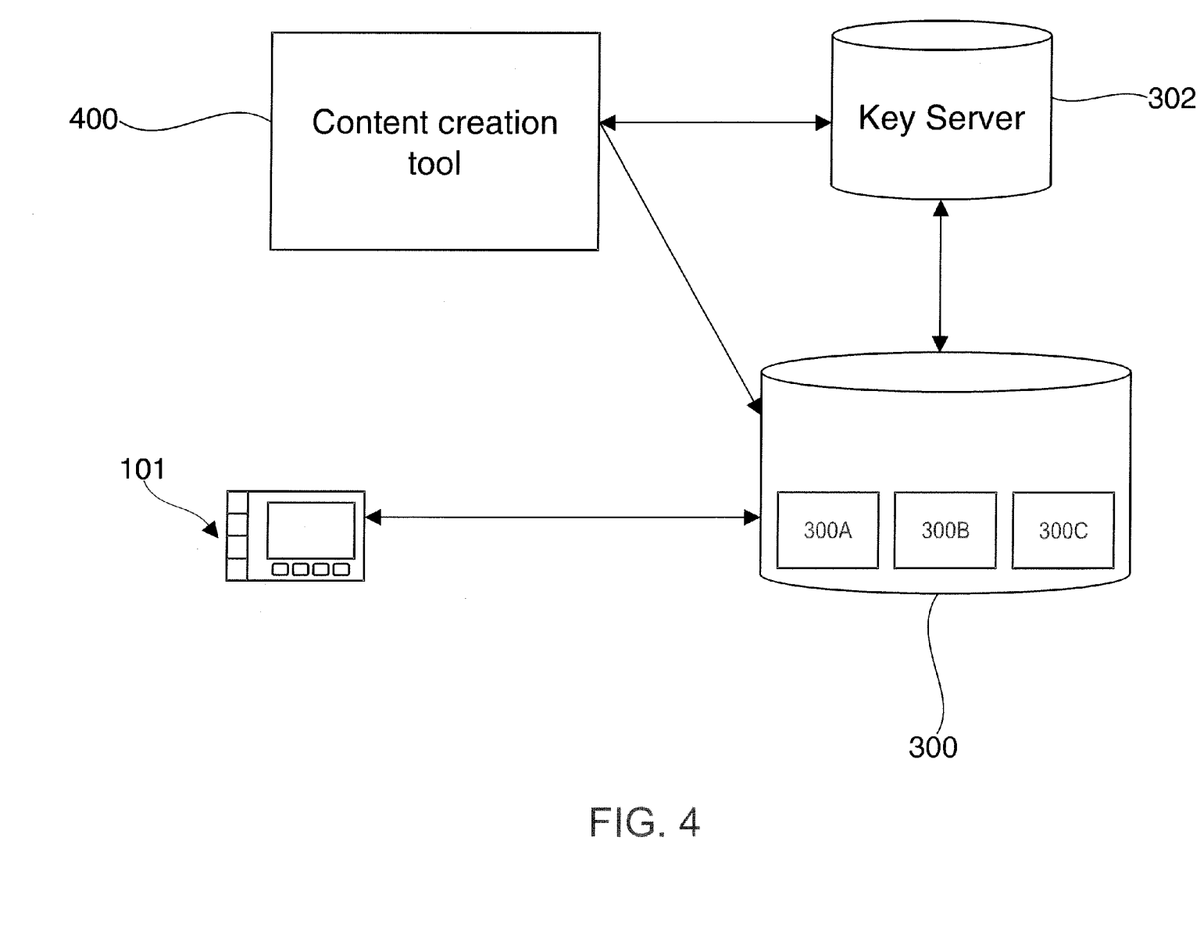
FIG. 4 illustrates a block diagram of a mechanism for creating authorized content in a medical device and recall management system according to an embodiment herein.

FIG. 4 illustrates a system for creating authorized content. A content creation tool 400 allows a content author to use scripting language and an authoring tool to compose scripted content for remote health management in a format operable on device 101 from any licensed manufacturer of a compatible design. Content creation tool 400 creates an encrypted binary version of program and an authentication key which is posted to key server 302. The binary version of content is hosted by service provider 300 for remote programming of medical device 101 and personalization through a data merged with the other data owned by the service provider 300. When the content is to be used by device 101, the embedded key must be confirmed by key server 302 that device 101 is authentic and the user is eligible to use program content. The eligibility is determined by the economic terms with the software provider and software recall status.

The system ensures the secure management of the content usage while allowing the end users to remain anonymous. The end user utilizes the content in medical device 101, and this use is recorded anonymously but at the same time is managed so tightly that the usage can be turned off when there is a problem. This is possible because the patient receives the content and transmits the personal data to the service provider server 300. The request to key server 302 is just a code message asking for a return key code, and no patient data or content is being exchanged.

Figure 5:
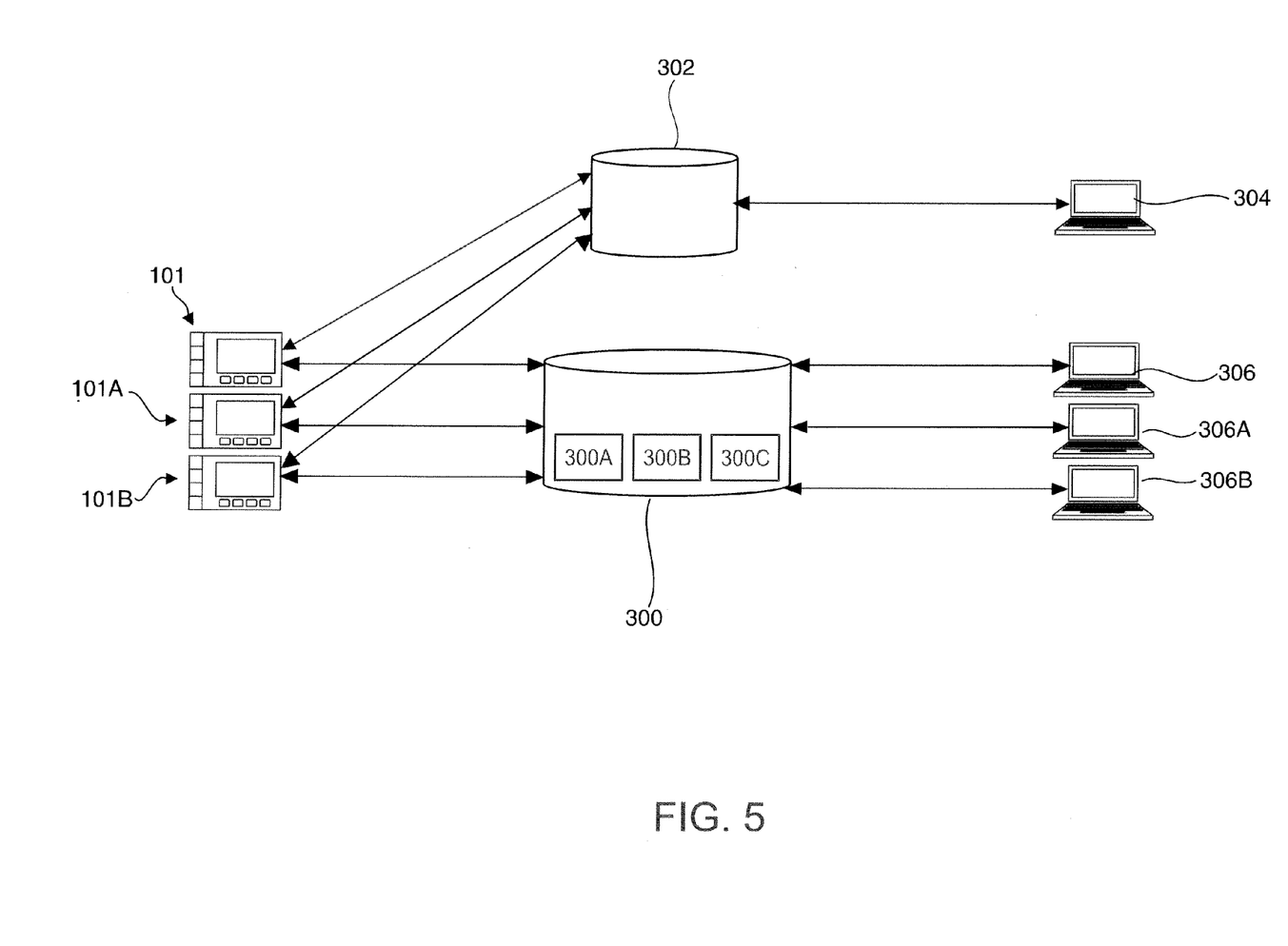
FIG. 5 illustrates a block diagram of a device-based authentication system for governing operation of medical device rights and recall management system according to an embodiment herein.

FIG. 5 illustrates a device-based authentication system for governing the operation of medical device rights and recall management. In this embodiment authentication is done in direct connection to the key server. In case of device-based authentication system for governing the operation of medical device 101, IP rights and recall manager 304 of medical device 101 has a separate and parallel transaction path with key server 302. Medical device 101 may receive content from the service provider server 300 connected to value-added service provider 306, 306A, 306B and may receive an authentication through a different transaction with the key server 302. Key server 302 validates medical device 101 and the embedded key based on received authentication data and the economic criteria to decode the software content and the services received from service provider server 300 provided with databases 300A, 300B, and 300C.

Figure 6:
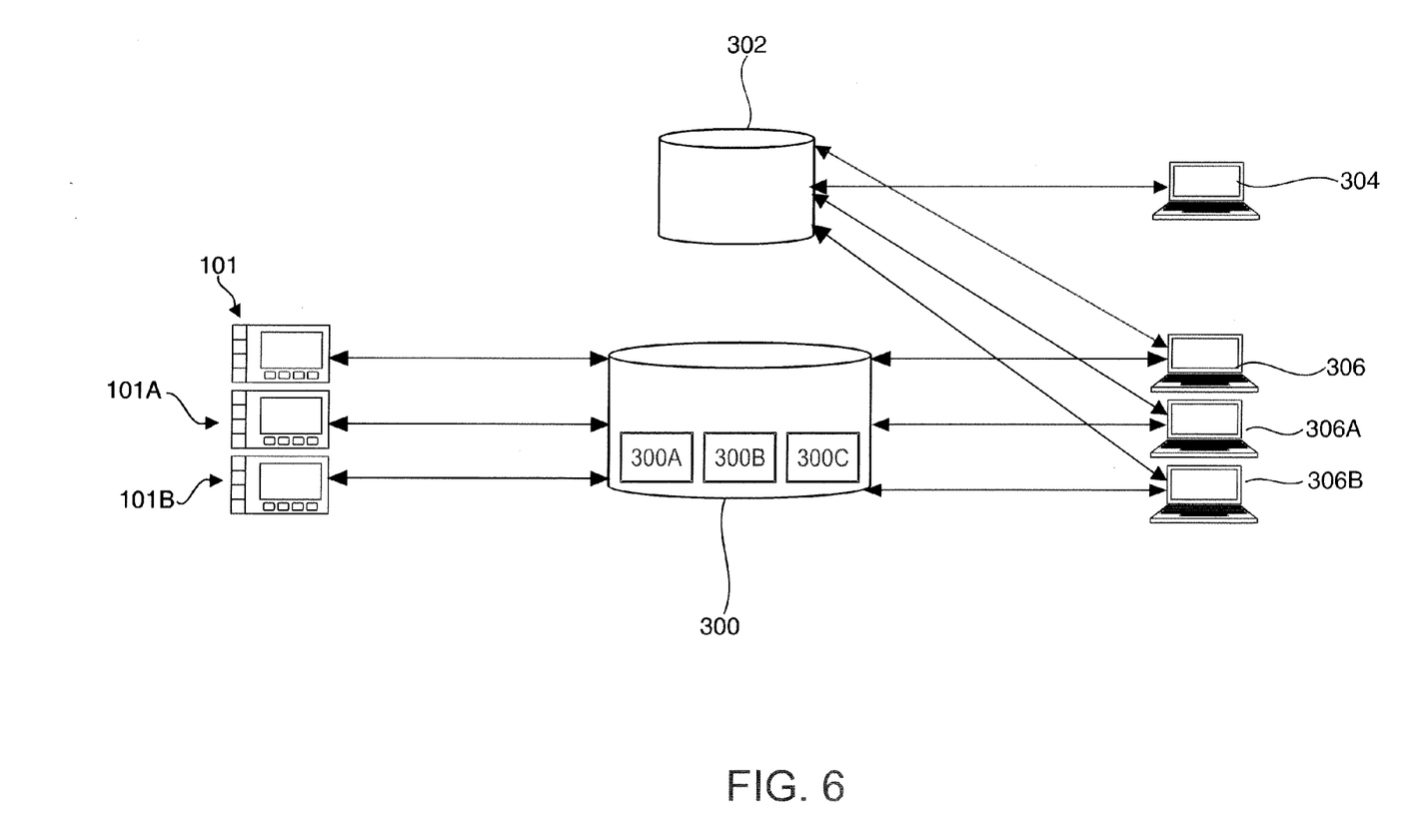
FIG. 6 illustrates a block diagram of a service-based authentication system for governing operation of medical device rights and recall management system according to an embodiment herein.

FIG. 6 illustrates a service-based authentication system for governing the operation of medical device rights and recall management. In case of service-based authentication system for governing the operation of medical device rights and recall management, services providers 306, 306A, 306B have a separate and parallel transaction path with a key server 302. Service providers 306, 306A, 306B receive the decoding key based on the authentication data received from the medical device through server 300 provided with databases 300A, 300B, 300C. Device IP rights management and recall device 304 is connected to key server 302 to activate key server 302 to issue the decoding key to service providers 306, 306A, 306B based on the successful verification of the authentication data of the medical device and the economic criteria.

Figure 7:
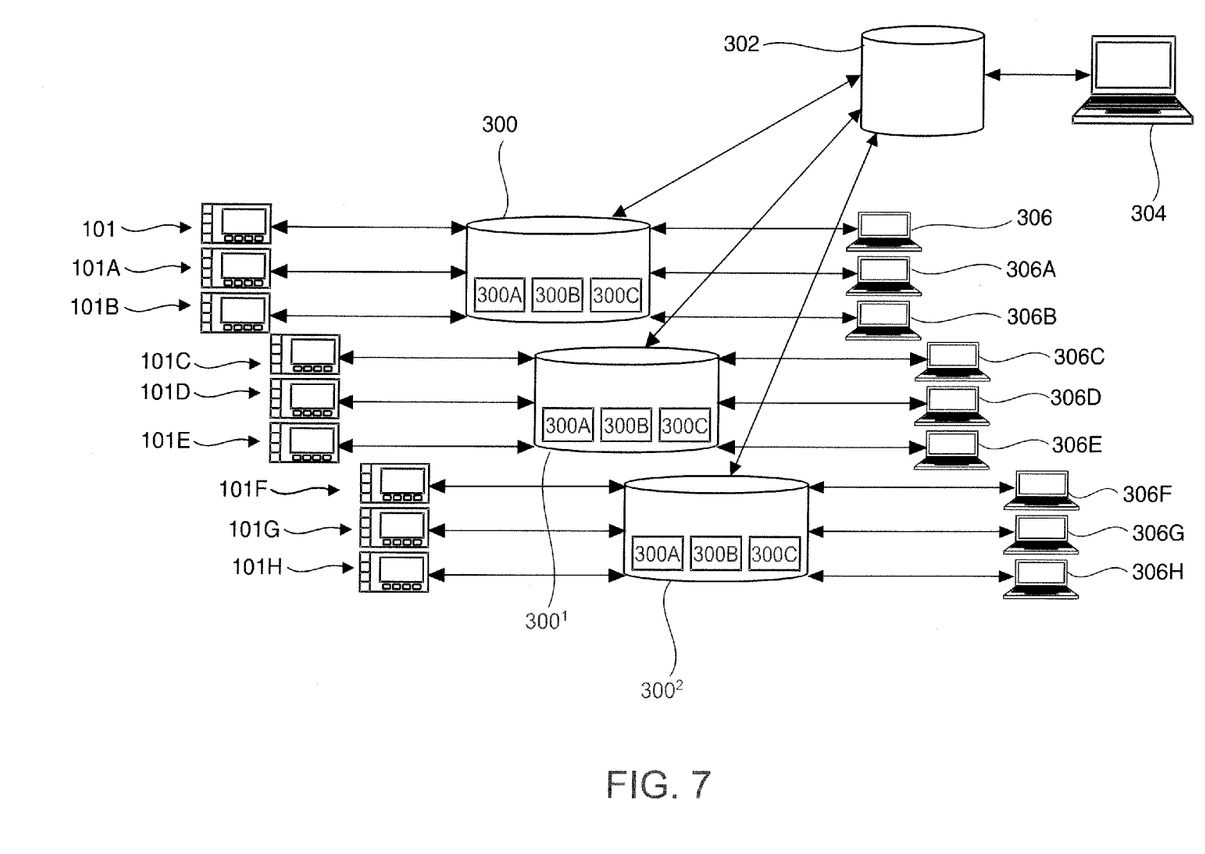
FIG. 7 illustrates a block diagram of a multiple licensed manufacturers and service providers for governing the operation of a medical device rights and recall management system according to an embodiment herein.

FIG. 7 illustrates an embodiment of the present embodiment using a server-to-server authentication network. A medical device rights and recalls management system for multiple licensed manufacturers and service providers managed by one digital rights manager 304. The content used by multiple service providers 306-306H is unlocked and logged in key server 302 through a transaction between the service provider server 300 and the key server 302 containing the master record. A recall may be demanded by the regulatory agency, if a failure is found in the software that needs to be corrected or disabled. Because the content author registers the content with key server 302, service content server 300 may have a virtual master device register for all software components regardless of service provider who uses the content. Because each of service provider servers 300, devices 101-101H, and caregiver computers 306-306H must register and obtain a key from key server 302, the system is able to manage and enforce a recall even though multiple service providers 306-306H are using content in multiple locations and programs. Since every content author registers the content with key server 302, the system keeps a virtual master device master record registered for all software components regardless of service provider 306-306H who uses the content. Because each of service provider servers 300, remote devices 101-101H, and caregiver computers 306-306H must register and obtain a key from key server 302, service provider server 300 may track, manage and enforce a recall even though multiple service providers 306-306H are using content in multiple locations and programs. Using the same approach, system ensures that the content author always gets credit even though the content is distributed through many different service providers 306-306H.

Figure 8:
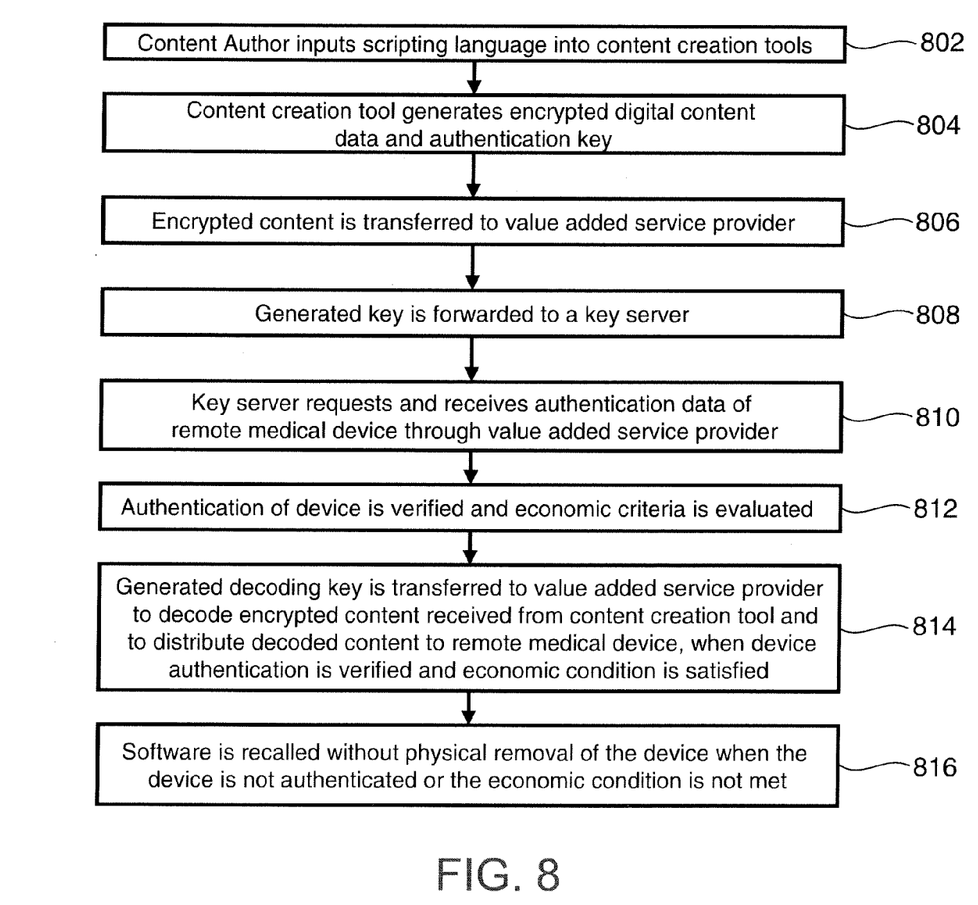
FIG. 8 illustrates a flowchart explaining the process by which a digital content is created using the medical device rights and recall management system according to one embodiment herein.

FIG. 8 illustrates a flowchart explaining the process by which a software content is created using the medical device rights and recall management system according to one embodiment herein. A content author inputs a scripting language into a content creation tool (802). The content author may be a third party software provider and value-added service provider. The content author is different from a device manufacturer or a primary service provider. Then the content creation tool is used to generate an encrypted digital content data and an authentication key used for decoding the encrypted digital content (804). The generated encrypted digital content is transferred to the server of value-added service provider (806). The generated authentication key is forwarded to a key server which is connected to the server of value-added service provider (808). The key server requests and receives the authentication data of a remote medical device requiring software content and services through the server of value-added service provider (810). The authentication of the device is checked and the economic criteria of the medical device are evaluated based on the received data by the key server (812). The generated authentication key is transferred to the server of the value-added service provider to decode the encrypted content received from the content creation tool and to distribute the decoded content and the services to the remote medical device, when the authentication of the remote medical device is verified successfully and the economic criteria is met (814). The software is recalled when the remote medical device is not authenticated and the economic criteria concerning the remote medical device is not met (816).

Figure 9:
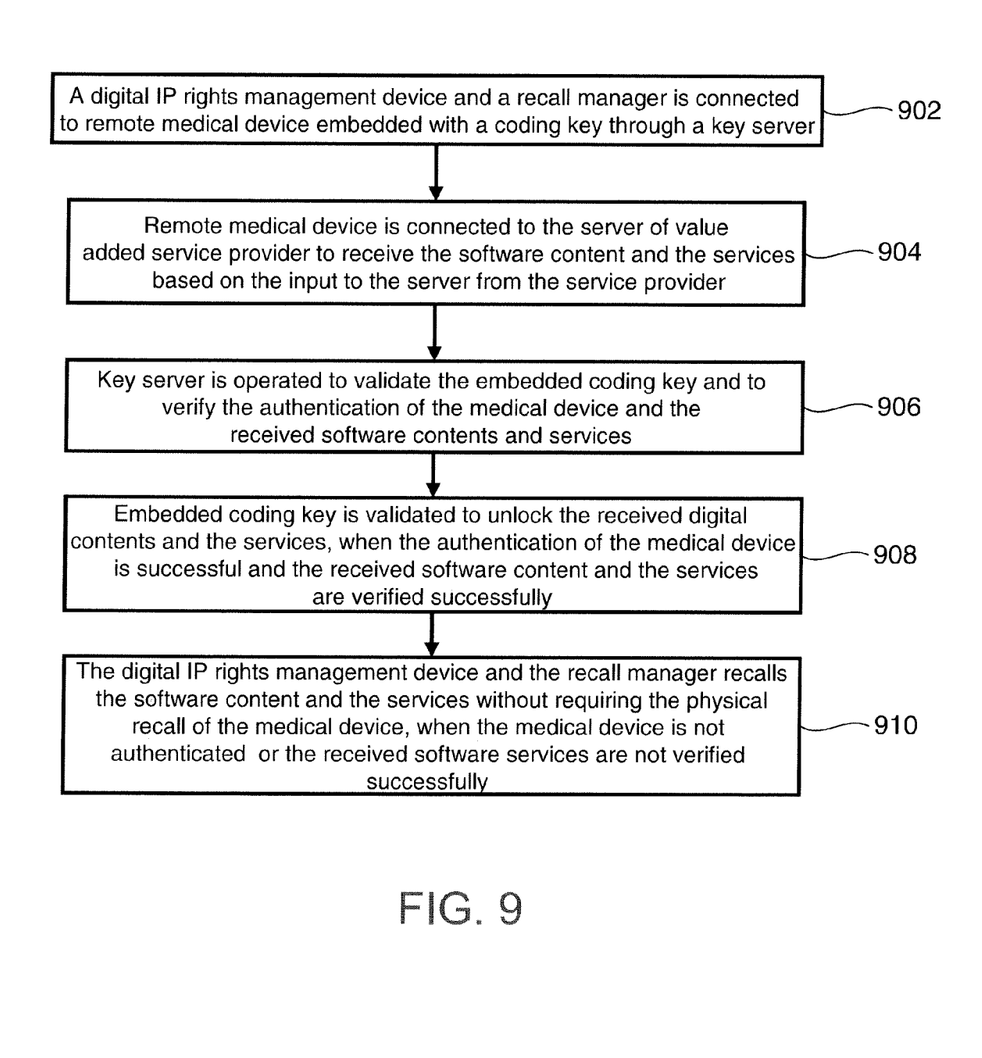
FIG. 9 illustrates a flowchart explaining the software recall management method using the medical device rights and recall management system according to one embodiment herein.

FIG. 9 illustrates a flow chart explaining the software recall management method using the medical device rights and recall management system according to one embodiment herein. According to the medical device rights and recall management system, a digital IP rights management and recall manager is connected to a key server to authenticate the software and the services operated on a remotely programmable and monitored medical device such as a patient device. The remote medical device is connected to the server of a value-added service provider to receive software content and services. The server of value-added service provider server is connected to the key server and to the computer of the value-added service provider or the end user who may be a customer to the value-added service provider.

The digital IP rights management device and recall manager activates a key server to authenticate the software and the services operated on the remote medical device (901). The key server searches for the coding key embedded in the remote medical device (902). When the key server detects the embedded coding key in the remote medical device, the key server authenticates the software and services that are received from the value-added service provider server and operated on the remote medical device (903). When the key server authenticates the software and the services successfully, the key server unlocks and decodes the software using the embedded coding key (904). When the key server could not authenticate the software and the services, then the digital IP rights management and recall manger recalls the software through key server without recalling the remote medical device physically (905).

When the key server could not detect the embedded coding key in the remote medical device, then the key server searches for the coding key embedded in the server of value-added service provider (906). When the key server detects the embedded coding key in the server of value-added service provider, the key server authenticates the remote medical device through the server of value-added service provider server. When the key server authenticates the remote medical device successfully, the key server permits the server of value-added service provider to transmit the software and the services to the remote medical device. The key server decodes and unlocks the software and the services using the coding key embedded in the server of value-added service provider for use in the remote medical device. When the remote medical device is not authenticated successfully, the software and the services are not transferred to the remote medical device and the software and the services are recalled without recalling the remote medical device physically.

When the key server could not detect the embedded coding key in the server of value-added service provider server, then the key server searches for the coding key embedded in the computer of value-added service provider or customer/end user (910). When the key server detects the coding key embedded in the computer of value-added service provider server or customer/end user, the key server authenticates the remote medical device through the computer of value-added service provider or customer/end user and the server of value-added service provider. When the key server authenticates the remote medical device successfully, the key server permits the value-added service provider to transmit the software and the services to the remote medical device through the server of value-added service provider. Then the key server unlocks the software and the services transmitted to the remote medical device from the value-added service provider using the coding key embedded in the computer of value-added service provider or customer/end user. When the key server could not authenticate the remote medical device successfully, the digital IP rights management device and recall manager recalls the software and the services operated on the remote medical device through the key server without recalling the remote medical device physically.

When the key server could not detect the embedded coding key in the computer of value-added service provider or customer/end user, the key server is made to restart the coding key searching process to search for the embedded coding key in remote medical device or server of value-added service provider or computer of value-added service provider or customer/end user.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A medical device rights and recall management system, comprising:
   a microprocessor based medical device comprising a sensor for collecting a data set about at least one of: a patient or an environment;
   a service provider device operably connected to said microprocessor based medical device, said service provider device supplying software for execution on said microprocessor based medical device, said service provider device configured for maintaining a virtual device master record, said service provider device further configured for anonymously tracking and managing transactions with the software;
   a content device for creating said software operably connected to said service provider device, the content device not in direct communication with the microprocessor based medical device;
   a coding key embedded in said microprocessor based medical device;
   a key server communicatively coupled to said microprocessor based medical device and to said service provider device; the key server for controlling data transfer between the microprocessor based medical device and the service provider device, the key server including a set of rules for how said software can be used; and
   an intellectual property rights management device communicatively connected to said key server, the intellectual property rights management device not in direct communication with the microprocessor based medical device;
   wherein the key server interrogates said intellectual property rights management device to validate the coding key embedded in said microprocessor based medical device and said intellectual property rights management device communicates a result of said interrogation to the service provider device, the result of said interrogation including a return key code indicating whether the microprocessor based medical device is authentic and a user of the microprocessor based medical device is eligible to use the software, thereby enabling the service provider device to selectively unlock and activate said software via the connection between the microprocessor based medical device and the service provider device.

2. The medical device rights and recall management system of claim 1, wherein the coding key is embedded in the service provider device.

3. The medical device rights and recall management system of claim 1, further comprising an end user device communicatively coupled to the service provider device and the intellectual property rights management device, wherein the coding key is embedded in the end user advice, the key server interrogates said intellectual property rights management device to validate the coding key embedded in said end user device by transmitting the coding key to the key server and said intellectual property rights management device validates the key and communicates a result of said interrogation to the service provider device including a return key code indicating whether the end user device is authentic and a user of the end user device is eligible to use the software, thereby enabling the service provider device to selectively unlock and activate said software via the connection between the end user device and the service provider device.

4. The medical device rights and recall management system of claim 1, wherein said content device is configured to use scripting language to compose the software in a pre-specified format.

5. The medical device rights and recall management system of claim 1, wherein said content device registers the software on the key server.

6. The medical device rights and recall management system of claim 1, wherein said software is used for value-added functions such as remote monitoring, patient guidance, education and feedback.

7. The medical device rights and recall management system as claimed in claim 1, wherein the data set about at least one of a patient comprises at least one of: a blood pressure, a blood glucose level, a pulse rate, a heart rate variability, a pulse oximeter level, a blood coagulation level, a respiratory condition, a body weight, or a body fat content of the patient.

8. The medical device rights and recall management system as claimed in claim 1, wherein the data set about at least one of a patient or an environment comprises at least one of: a smoke level, a gas level, a humidity level, or an indication of the presence of a fire.

9. A software recall management method in a medical device rights and recall management system, comprising the steps of:
   providing a microprocessor based medical device configured to receive at least one of a service or software; the microprocessor based medical device further comprising a sensor for collecting a data set about at least one of a patient or an environment;
   embedding a coding key in the microprocessor based medical device;
   communicatively connecting a service provider device to the microprocessor based medical device, the service provider device supplying software for execution on the microprocessor based medical device;
   communicatively connecting a key server to the microprocessor based medical device and to the service provider device, the key server including a set of rules for how said software can be used;
   communicatively connecting an intellectual property rights management device to the key server;
   interrogating the intellectual property rights management device to validate the coding key embedded in the microprocessor based medical device, said interrogation including a determination if the microprocessor based medical device is authentic and a user of the microprocessor based medical device is eligible to use the software;
   authenticating the coding key through the key server operated by the intellectual property rights management device;
   communicating a result of said interrogation to the service provider device, the result of said interrogation including a return key code, the result of said interrogation completed without exchanging any data from the data set with the microprocessor based medical device;
   selectively unlocking and activating the software via the connection between the microprocessor based medical device and the service provider device; and
   anonymously tracking transactions with the software without accessing the data set or the software.

10. The method according to claim 9, wherein the intellectual property rights management device validates said coding key and enables said microprocessor based medical device to unlock content transmitted to or from the service provider.

11. The method according to claim 9, wherein the coding key is embedded in the service provider server.

12. The method according to claim 9, wherein the coding key is embedded in an end user computer that is connected to the service provider device to access the data set collected through said microprocessor based medical device.

13. The method according to claim 9, wherein a virtual device master record is kept to achieve quality control and recall capability of the software independent of any physical recall of the microprocessor based medical device.

* * * * *